United States Patent
Zheng et al.

(10) Patent No.: US 12,260,636 B1
(45) Date of Patent: Mar. 25, 2025

(54) DECISION-MAKING METHOD AND APPARATUS FOR WATER AND FERTILIZER STRESS OF CROPS, AND MOBILE PHONE TERMINAL

(71) Applicant: INTELLIGENT EQUIPMENT RESEARCH CENTER, BEIJING ACADEMY OF AGRICULTURE AND FORESTRY SCIENCES, Beijing (CN)

(72) Inventors: Wengang Zheng, Beijing (CN); Zhonglili Zhang, Beijing (CN); Chunjiang Zhao, Beijing (CN); Liping Chen, Beijing (CN); Shirui Zhang, Beijing (CN); Xin Zhang, Beijing (CN); Xinyue Lv, Beijing (CN)

(73) Assignee: INTELLIGENT EQUIPMENT RESEARCH CENTER, BEIJING ACADEMY OF AGRICULTURE AND FORESTRY SCIENCES, Beijing (CN)

( * ) Notice: Subject to any disclaimer, the term of this patent is extended or adjusted under 35 U.S.C. 154(b) by 0 days.

(21) Appl. No.: 18/286,235

(22) PCT Filed: Jul. 27, 2023

(86) PCT No.: PCT/CN2023/109528
§ 371 (c)(1),
(2) Date: Oct. 10, 2023

(87) PCT Pub. No.: WO2024/178904
PCT Pub. Date: Sep. 6, 2024

(30) Foreign Application Priority Data

Feb. 28, 2023 (CN) .................. 202310173436.X

(51) Int. Cl.
*G06V 20/10* (2022.01)
*G01N 33/00* (2006.01)
(Continued)

(52) U.S. Cl.
CPC ....... *G06V 20/188* (2022.01); *G01N 33/0098* (2013.01); *G06T 7/0012* (2013.01);
(Continued)

(58) Field of Classification Search
CPC ...... G06V 20/188; G06V 20/68; G06V 20/70; G06V 10/765; G06T 7/11; G06T 7/174;
(Continued)

(56) References Cited

U.S. PATENT DOCUMENTS 8,924,031 B1 12/2014 Evett et al.
2016/0183483 A1* 6/2016 Motohari Sharif .. A01G 25/165
700/284

FOREIGN PATENT DOCUMENTS

CN 108323295 A 7/2018
CN 112488230 A 3/2021
(Continued)

OTHER PUBLICATIONS

Mendes et al. NPL "Smartphone Applications Targeting Precision Agriculture Practices—A Systematic Review" (Year: 2020).*
(Continued)

*Primary Examiner* — Jonathan S Lee
*Assistant Examiner* — Winta Gebreslassie
(74) *Attorney, Agent, or Firm* — Gearhart Law, LLC

(57) ABSTRACT

The present disclosure provides a decision-making method and apparatus for water and fertilizer stress of crops, and a mobile phone terminal, and belongs to the technical field of intelligent agriculture. The method includes: determining a current crop coefficient and canopy temperature of a crop to be identified on the basis of a first crop image and a second
(Continued)

crop image; determining a water stress state and a nutrient stress state on the basis of the current crop coefficient and canopy temperature of the crop to be identified; and processing the water stress state and the nutrient stress state with a fuzzy control algorithm, and determining a water and fertilizer stress decision result of the crop to be identified.

19 Claims, 4 Drawing Sheets

(51) Int. Cl.
  *G06T 7/00* (2017.01)
  *G06T 7/11* (2017.01)
  *G06T 7/174* (2017.01)
  *G06V 10/764* (2022.01)
  *G06V 20/68* (2022.01)
  *G06V 20/70* (2022.01)
(52) U.S. Cl.
  CPC .............. *G06T 7/11* (2017.01); *G06T 7/174* (2017.01); *G06V 10/765* (2022.01); *G06V 20/68* (2022.01); *G06V 20/70* (2022.01); *G06T 2207/10048* (2013.01); *G06T 2207/30004* (2013.01); *G06T 2207/30188* (2013.01)
(58) Field of Classification Search
  CPC ......... G06T 7/0012; G06T 2207/10048; G06T 2207/30004; G06T 2207/30188; G01N 33/0098

See application file for complete search history.

(56) References Cited

FOREIGN PATENT DOCUMENTS

| | | |
|---|---|---|
| CN | 114662742 A | 6/2022 |
| CN | 115861827 A | 3/2023 |
| WO | 2019109383 A1 | 6/2019 |

OTHER PUBLICATIONS

International Search Report received in International Application No. PCT/CN2023/109528, mailed on Nov. 2, 2023, 3 Pages.

He et al., "Study on water stress index model of lettuce based on fusion of thermal infrared and visible light images", Water Saving Irrigation, vol. 3, 2023, pp. 116-122 (English Abstract).

First office action received in CN Application No. 202310173436.X, Dated Mar. 31, 2023, pp. 14 including English translation.

Notification to Grant patent right for Invention in CN Application No. 202310173436.X, Dated Apr. 26, 2023, pp. 3 including English translation.

* cited by examiner

DECISION-MAKING METHOD AND APPARATUS FOR WATER AND FERTILIZER STRESS OF CROPS, AND MOBILE PHONE TERMINAL

CROSS REFERENCE TO RELATED APPLICATION

The present is a national stage application of International Patent Application No. PCT/CN2023/109528, filed on Jul. 27, 2023, which application claims the priority to Chinese Patent Application No. 202310173436.X, filed with the China National Intellectual Property Administration on Feb. 28, 2023 and entitled "DECISION-MAKING METHOD AND APPARATUS FOR WATER AND FERTILIZER STRESS OF CROPS, AND MOBILE PHONE TERMINAL", which is incorporated in their entireties herein by reference.

TECHNICAL FIELD

The present disclosure relates to the technical field of intelligent agriculture, and particularly relates to a decision-making method and apparatus for water and fertilizer stress of crops, and a mobile phone terminal.

BACKGROUND

Management of water and nutrients is crucial to agricultural production, with influence on yield and quality of crops. Through rational combined application of water and fertilizers, agricultural irrigation water can be rationally reduced, and fertilizers can be applied as required. Accordingly, water and nutrients can be concentrated in a crop root zone to accurately satisfy demand of crops. Further, excessive resource consumption is reduced, and agricultural production potential is improved. It is of great significance for saving resources and protecting the environment. But in practice, local planting managers generally irrigate crops with water and fertilizers empirically. In the absence of diagnosis of actual crop growth, widespread use of such an empirical way in planting production is impossible. As a consequence, it is necessary to diagnose a water and fertilizer stress state and make a decision about irrigation on the basis of crop growth information parameters obtained from image processing and expertise.

In the prior art, water and fertilizers are merely diagnosed but not collaboratively decided in most cases. In addition, the problem of low temperature extraction accuracy has been found during water deficit diagnosis with a thermal infrared image. A variety of devices are required for collecting thermal infrared images and visible light images, which leads to high cost, low flexibility and narrow application range.

SUMMARY

The present disclosure provides a decision-making method and apparatus for water and fertilizer stress of crops, and a mobile phone terminal, so as to solve a problem that crops cannot be cultivated accurately without collaborative water and fertilizer decision-making in the prior art.

The present disclosure provides a decision-making method for water and fertilizer stress of crops. The method includes:

determining a current crop coefficient and canopy temperature of a crop to be identified on the basis of a first crop image and a second crop image;

determining a water stress state and a nutrient stress state on the basis of the current crop coefficient and canopy temperature of the crop to be identified; and processing the water stress state and the nutrient stress state with a fuzzy control algorithm, and determining a water and fertilizer stress decision result of the crop to be identified.

The water and fertilizer stress decision result includes an irrigation amount and/or a topdressing amount for the crop to be identified in a next cycle. The first crop image is a visible light image obtained by photographing the crop to be identified in full view with a terminal. The second crop image is a thermal infrared image obtained by photographing the crop to be identified in full view with an infrared module connected to the terminal.

In the decision-making method for water and fertilizer stress of crops according to the present disclosure, the processing the water stress state and the nutrient stress state with a fuzzy control algorithm, and determining a water and fertilizer stress decision result of the crop to be identified includes:

converting the water stress state and the nutrient stress state into linguistic variables, inputting the linguistic variables into a fuzzy controller, and obtaining an irrigation instruction output from the fuzzy controller;

setting, in response to determining that first identifier information and second identifier information that are carried by the irrigation instruction are non-null and null respectively, an irrigation amount determined according to the crop coefficient and a reference crop evapotranspiration amount as the water and fertilizer stress decision result;

setting, in response to determining that first identifier information and second identifier information that are carried by the irrigation instruction are null and non-null respectively, a topdressing amount determined according to the nutrient stress state and species information of the crop to be identified as the water and fertilizer stress decision result; and setting, in response to determining that neither of first identifier information and second identifier information that are carried by the irrigation instruction is null, an irrigation amount determined according to the crop coefficient and a reference crop evapotranspiration amount and a topdressing amount determined according to the nutrient stress state and species information of the crop to be identified as the water and fertilizer stress decision result.

The fuzzy controller is created on the basis of a corresponding fuzzy rule between an input fuzzy set and an output fuzzy set. The input fuzzy set is determined according to a membership function set on the basis of fuzzy scales obtained by conducting fuzzy division on the water stress state and the nutrient stress state. The output fuzzy set is determined according to a membership function set on the basis of strategy scales of a plurality of water and fertilizer stress states obtained by clarifying a fuzzy language. The fuzzy rule is created by determining corresponding water and fertilizer stress states according to different water stress states and nutrient stress states. Identifier information carried by the irrigation instruction is determined according to the water and fertilizer stress state. The first identifier information is configured to indicate whether to conduct irrigation. The second identifier information is configured to indicate whether to conduct topdressing.

In the decision-making method and apparatus for water and fertilizer stress of crops and the mobile phone terminal according to the present disclosure, image features of a canopy zone are extracted according to the first crop image and the second crop image collected by the mobile phone terminal having a thermal infrared imaging function, the water stress state and the nutrient stress state are diagnosed according to the extracted crop coefficient and canopy temperature, respectively, collaborative decision-making is conducted on the water stress state and the nutrient stress state with the fuzzy control algorithm, and the irrigation amount of the water and the fertilizers in the next cycle is output as the water and fertilizer stress decision result. The present disclosure can achieve dynamic collaborative water and fertilizer diagnosis and decision-making by combining image processing related algorithms, fuzzy control and expertise through an image collection means having high flexibility and low cost.

BRIEF DESCRIPTION OF THE DRAWINGS

To describe technical solutions of the present disclosure or in the prior art more clearly, the accompanying drawings required for describing embodiments or the prior art will be briefly described below. Obviously, the accompanying drawings in the following description show some embodiments of the present disclosure, and those of ordinary skill in the art can still derive other drawings from these accompanying drawings without inventive effort.

DETAILED DESCRIPTION OF THE EMBODIMENTS

To make objectives, technical solutions and advantages of the present disclosure clearer, the technical solutions of the present disclosure will be clearly and completely described below in conjunction with the accompanying drawings of the present disclosure. Obviously, the described embodiments are some embodiments rather than all embodiments of the present disclosure. Based on the embodiments of the present disclosure, all the other embodiments obtained by those of ordinary skill in the art without inventive effort fall within the protection scope of the present disclosure.

The terms such as "first" and "second" in the present application are used to distinguish between similar objects and are not intended to describe a specific order or sequence. It should be understood that data used in such a way may be interchanged under appropriate circumstances such that the embodiments of the present application can be implemented in an order other than those illustrated or described herein, the objects distinguished by "first", "second", etc. are generally of the same type, and the number of objects is not limited. For example, one or more first objects may exist.

It should be understood that the terms used in the description of the present disclosure are for the purpose of describing specific embodiments only and are not intended to limit the present disclosure. As used in the present disclosure, the singular forms "a", "an", "one" and "the" are intended to include the plural forms unless otherwise explicitly indicated in the context.

The terms "include" and "comprise" indicate the existence of the described feature, entity, step, operation, element and/or assembly, but do not exclude the existence or addition of one or more other features, entities, steps, operations, elements, assemblies and/or their combination.

Figure 1:
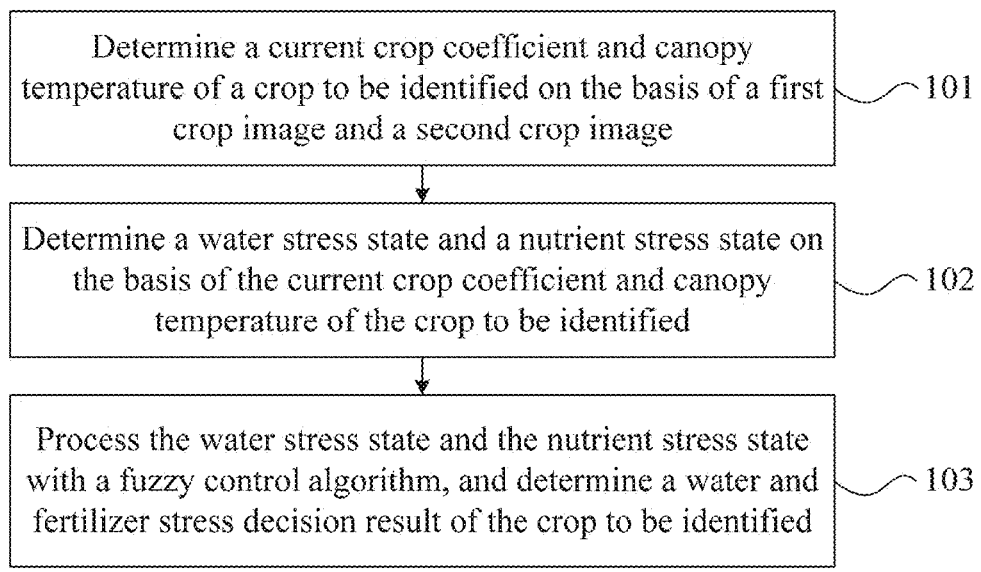
FIG. 1 is a first schematic flow diagram of a decision-making method for water and fertilizer stress of crops according to the present disclosure.

FIG. 1 is a first schematic flow diagram of a decision-making method for water and fertilizer stress of crops according to the present disclosure. As shown in FIG. 1, the decision-making method for water and fertilizer stress of crops according to an embodiment of the present disclosure includes the following steps:

Step 101, a current crop coefficient and canopy temperature of a crop to be identified are determined on the basis of a first crop image and a second crop image.

The first crop image is a visible light image obtained by photographing the crop to be identified in full view with a terminal. The second crop image is a thermal infrared image obtained by photographing the crop to be identified in full view with an infrared module connected to the terminal.

It should be noted that an execution entity of the decision-making method for water and fertilizer stress of crops according to the embodiment of the present disclosure is a decision-making apparatus for water and fertilizer stress of crops.

The decision-making method for water and fertilizer stress of crops according to the embodiment of the present application is suitable for a user to use an electronic device to process an image obtained by photographing a crop with a mobile phone terminal, and to identify and make a decision on a water and fertilizer stress state according to a feature identified from the image.

At specified time intervals, the mobile phone terminal collects image information including the crop to be identified in full view under visible light in cycles, and transmits the image information as the first crop image to the decision-making apparatus for water and fertilizer stress of crops.

An infrared module in communication connection with a mobile phone terminal body is driven to collect image information including the crop to be identified in full view under thermal infrared light in the same field of view while a photographing module of the mobile phone terminal body collects the visible light image, and transmits the image information as the second crop image to the decision-making apparatus for water and fertilizer stress of crops.

In addition, the electronic device may be implemented in various forms. For example, the electronic devices described in the embodiment of the present disclosure may include mobile terminals such as a mobile phone, a smart phone and a notebook computer and fixed terminals such as a desktop computer. It is assumed that the electronic device is a mobile terminal below. However, those skilled in the art may understand that a configuration according to the embodiment of the present application may also be applied to a fixed terminal, in addition to elements specifically for mobile purposes.

Specifically, in step 101, the decision-making apparatus for water and fertilizer stress of crops receives the first crop image and the second crop image collected by the photographing module and the infrared module arranged on the mobile phone terminal in a current working cycle respectively, conducts a related image algorithm on the received images, and completely separates a canopy zone of the crop. Further, the crop coefficient and canopy temperature corresponding to each pixel point in the canopy zone are converted.

The crop coefficient refers to a ratio of a water demand to a possible evapotranspiration amount of the crop in different development stages, and is generally expressed as $K_c$. According to a change rule in a crop growth process, the crop coefficient changes from small to large in an early stage, is maximized in a vigorous growth period, and gradually decreases in a later stage.

It may be understood that perspective distortion and three-dimensional distortion caused when a phone photographs an image are avoided through a perspective transformation method. Perspective transformation is a three-dimensional image conversion process to project an image onto a new visual plane. Coordinates of a set of four points in a collected image and a set of four points in a target image are taken, and a distorted image is corrected through perspective transformation. A transformation matrix of perspective transformation is computed according to two sets of coordinate points, and further an entire original image is transformed, such that a first corrected crop image is obtained.

Step 102, a water stress state and a nutrient stress state are determined on the basis of the current crop coefficient and canopy temperature of the crop to be identified.

Specifically, in step 102, the decision-making apparatus for water and fertilizer stress of crops converts and maps influence of objective factors such as a climate condition, groundwater drought and a plant root size on crop water management to the water stress state according to the ratio of the water demand to the possible evapotranspiration amount and outputs the water stress state. The ratio is denoted by the crop coefficient obtained in step 101.

Meanwhile, influence of crop genetic characteristics and environmental conditions on crop nutrient management is converted and mapped to the nutrient stress state according to a thermodynamic state of surface vegetation denoted by the canopy temperature obtained in step 101, and the nutrient stress state is output.

Step 103, the water stress state and the nutrient stress state are processed with a fuzzy control algorithm, and a water and fertilizer stress decision result of the crop to be identified is determined.

The water and fertilizer stress decision result includes an irrigation amount and/or a topdressing amount for the crop to be identified in a next cycle.

Specifically, in step 103, the decision-making apparatus for water and fertilizer stress of crops determines each irrigation decision index under combined action of the water stress state and the nutrient stress state with a membership function in the fuzzy control algorithm, and further conducts irrigation decision-making with a pre-created fuzzy rule, so as to obtain the water and fertilizer stress decision result of the crop to be identified.

The water and fertilizer stress decision result is determined according to a fuzzy rule that may balance water and fertilizers at a basic level in the next cycle.

If a rule triggered by the water stress state and the nutrient stress state in a current cycle indicates that irrigation needs to be conducted for achieving basic balance of the water and the fertilizers, the water and fertilizer stress decision result only includes the irrigation amount of the crop in the next cycle.

If a rule triggered by the water stress state and the nutrient stress state in a current cycle indicates that topdressing needs to be conducted for achieving basic balance of the water and the fertilizers, the water and fertilizer stress decision result only includes the topdressing amount for the crop in the next cycle.

If a rule triggered by the water stress state and the nutrient stress state in a current cycle indicates that irrigation and topdressing need to be conducted at the same time for achieving basic balance of the water and the fertilizers, the water and fertilizer stress decision result includes the irrigation amount and the topdressing amount for the crop in the next cycle.

In the prior art, in order to obtain the visible light image and the thermal infrared image of the crop, various devices are required to collect images, which leads to high device cost and difficulty in obtaining images. Moreover, experimental research on water and fertilizer decision-making conducts diagnosis mainly according to experience, in lack of collaborative water and fertilizer decision-making and irrigation. Limited by difficulty in obtaining experimental data, most experiments in existing research conduct water and fertilizer decision-making and irrigation according to years of planting experience, which requires extensive experimental research for different crops. A large amount of manpower is required for the research under limited experimental conditions, and further the research can be hardly applied to mass production and planting of crops.

The present application obtains a crop image only with a portable configuration, for example, a smart phone terminal having a thermal imaging technology, such that image data is more flexible and convenient to obtain, and input cost is lower. Meanwhile, the present application is highly flexible and easy to carry around. Whether to conduct water and fertilizer irrigation is diagnosed with the fuzzy control algorithm, and the irrigation amount of the water and the fertilizers is converted by combining prior data, such that real-time collaborative water and fertilizer diagnosis is achieved, and a traditional method for conducting water and fertilizer irrigation on the basis of experience in a planting process is innovatively changed.

According to the embodiment of the present disclosure, image features of the canopy zone are extracted according to the first crop image and the second crop image collected by the mobile phone terminal having a thermal infrared imaging function, the water stress state and the nutrient stress state are diagnosed according to the extracted crop coefficient and canopy temperature respectively, collaborative decision-making is conducted on the water stress state and the nutrient stress state with the fuzzy control algorithm, and the irrigation amount of the water and the fertilizers in the next cycle is output as the water and fertilizer stress decision result. The present disclosure can achieve dynamic collaborative water and fertilizer diagnosis and decision-making by combining image processing related algorithms, fuzzy control and expertise through an image collection means having high flexibility and low cost.

On the basis of any one of the above embodiments, the steps that the water stress state and the nutrient stress state are processed with the fuzzy control algorithm, and the water and fertilizer stress decision result of the crop to be identified is determined include the following steps: the water stress state and the nutrient stress state are converted into linguistic variables, the linguistic variables are input into a fuzzy controller, and an irrigation instruction output from the fuzzy controller is obtained.

The fuzzy controller is created on the basis of a corresponding fuzzy rule between an input fuzzy set and an output fuzzy set. The input fuzzy set is determined according to a membership function set on the basis of fuzzy scales obtained by conducting fuzzy division on the water stress state and the nutrient stress state. The output fuzzy set is determined according to a membership function set on the basis of strategy scales of a plurality of water and fertilizer stress states obtained by clarifying a fuzzy language. The fuzzy rule is created by determining corresponding water and fertilizer stress states according to different water stress states and nutrient stress states. Identifier information carried by the irrigation instruction is determined according to the water and fertilizer stress state.

Specifically, in step 103, considering that irrigation decision-making is influenced by many environmental factors and has uncertainty in crop irrigation, the decision-making apparatus for water and fertilizer stress of crops introduces and describes a fuzzy decision-making method. That is, input of the controller is set as the linguistic variables corresponding to the water stress state and the nutrient stress state, and output of the controller is the irrigation instruction configured to instruct irrigation of the water and/or the fertilizers.

A fuzzy set theory is a representation for converting a binary relation to continuous uncertainty and evaluating the continuous uncertainty with a correlation function. A set in a classical theory is a clearly defined boundary having only two states, 0 or 1. However, in consideration of the fact that irrigation decision-making is influenced by many environmental factors and has uncertainty in crop irrigation, the fuzzy set theory is introduced to define the input fuzzy set and the output fuzzy set. According to thresholds under different water and fertilizer states in Table 1, a fuzzy scale division method of each variable is as follows.

TABLE 1

Schematic table of thresholds of water and fertilizers under different stress states

| \ | Threshold | | |
|---|---|---|---|
| | Normal state | Moderate state | Stressedstate |
| Water | 0.3 | 0.3-0.65 | 0.65 |
| Fertilizer | 0.5 | 0.3-0.5 | 0.3 |

An interval in which a water stress state is smaller than 0.3 is regarded as a normal state, an interval from 0.3 to 0.65 is regarded as a moderate state, and an interval greater than 0.65 is regarded as a stressed state. That is, the water stress state is divided into three fuzzy subsets: N (normal state), M (moderate state) and P (stressed state), with a value range of [0,1].

An interval in which a nutrient stress state is greater than 0.5 is regarded as a normal state, an interval from 0.3 to 0.5 is regarded as a moderate state, and an interval smaller than 0.3 is regarded as a stressed state. That is, the nutrient stress state is divided into three fuzzy subsets: N (normal state), M (moderate state) and P (stressed state), with a value range of [0,1].

In order to improve computation efficiency, the water and fertilizer stress state after output and collaboration is also set as a set consisting of 3 fuzzy subsets: {N (more fertilizers and less water), M (water and fertilizers equal in amount), and P (more water and less fertilizers)}.

Further, the membership function is defined according to the fuzzy scales including all indexes. A one-dimensional membership function includes, but is not limited to, a triangular membership function, a trapezoidal membership function, a Gaussian function, and a bell-shaped membership function. The embodiment of the present disclosure has no specific limit on the membership function.

For example, the embodiment of the present disclosure determines each irrigation decision index with the triangular membership function.

Then, fuzzy decision-making is conducted. A control rule is expressed as a general fuzzy relation R:

$$R = \left| \bigcup_{i=1}^{n} R_i \right| = \left| \bigcup_{i=1}^{n} (E_i \times U_i) \right| \quad (1)$$

$R_i$ denotes a fuzzy relation of an ith rule. i=1, 2, ... n, and n denotes the number of rules.

A fuzzy set for controlling U is output as:

$$U=(E\lambda EC)_i^T \circ R \quad (2)$$

∘ denotes a matrix product symbol.

According to membership degrees of fuzzy variables E, EC and U, in combination with a fuzzy control rule table, each corresponding controlled quantity is obtained according to formulas (1) and (2) and a maximum membership function principle, and further a decision rule of an irrigation fuzzy controller may be obtained.

TABLE 2

Schematic table of a water and fertilizer fuzzy decision rule

| Strategy | | Water | | |
|---|---|---|---|---|
| | | N | M | P |
| Fertilizer | N | M | M | N |
| | M | M | M | N |
| | P | P | P | M |

Whether to conduct irrigation is decided on the basis of the above decision rule obtained through fuzzy decision. If a strategy scale of a triggered decision rule is P, that is, a current irrigation decision indicates more fertilizers and less water, the irrigation instruction is set as topdressing without watering.

If a strategy scale of a triggered decision rule is M, that is, a current irrigation decision indicates water and fertilizers equal in amount, the irrigation instruction is set as topdressing and watering.

If a strategy scale of a triggered decision rule is N, that is, a current irrigation decision indicates more water and less fertilizers, the irrigation instruction is set as watering without topdressing.

In response to determining that first identifier information and second identifier information that are carried by the irrigation instruction are non-null and null respectively, an irrigation amount determined according to the crop coefficient and a reference crop evapotranspiration amount is set as the water and fertilizer stress decision result.

In response to determining that first identifier information and second identifier information that are carried by the irrigation instruction are null and non-null respectively, a topdressing amount determined according to the nutrient stress state and species information of the crop to be identified is set as the water and fertilizer stress decision result.

In response to determining that neither of first identifier information and second identifier information that are carried by the irrigation instruction is null, an irrigation amount determined according to the crop coefficient and a reference crop evapotranspiration amount and a topdressing amount determined according to the nutrient stress state and species information of the crop to be identified are set as the water and fertilizer stress decision result.

The first identifier information is configured to indicate whether to conduct irrigation. The second identifier information is configured to indicate whether to conduct topdressing.

It should be noted that the irrigation instruction is divided into the first identifier information indicating whether to conduct watering and the second identifier information indicating whether to conduct fertilization, and a water and fertilizer irrigation strategy is denoted by assigning values to the above identifier information.

Specifically, the decision-making apparatus for water and fertilizer stress of crops analyzes the irrigation instruction output from the fuzzy controller as follows:

If the first identifier information and the second identifier information that are carried by the irrigation instruction are non-null and null respectively, that is, the current irrigation decision indicates more water and less fertilizers, and only watering without topdressing is required, the irrigation amount is converted according to the crop coefficient and the reference crop evapotranspiration amount obtained in step 101, and the irrigation amount is regarded as the water and fertilizer stress decision result to be output. A computation formula of the irrigation amount $ET_c$ is:

$$ET_c = K_c * ET_0 \quad (3)$$

$ET_0$ is the reference crop evapotranspiration amount, and reflects influence of a weather condition on evaporation and transpiration. $K_c$ is the crop coefficient.

If the first identifier information and the second identifier information that are carried by the irrigation instruction are null and non-null respectively, that is, the current irrigation decision indicates more fertilizers and less water, and only topdressing without watering is required, the topdressing amount is converted according to the nutrient stress state obtained in step 102 and an empirical value of a fertilization amount summarized by experts in advance from the species information of the crop to be identified, and the top dressing amount is regarded as the water and fertilizer stress decision result to be output. The embodiment of the present disclosure has no specific limit on a method for determining the topdressing amount.

For example, with lettuce, wheat and Chinese cabbage as examples, a mapping relation between different nutrient stress states and different crop varieties with respect to the topdressing amount is shown in the following table.

TABLE 3

Schematic table of a mapping relation of a topdressing amount

| \ | Lettuce | wheat | Chinese cabbage |
|---|---|---|---|
| [0.5, 1) | 0-90 kg · hm$^{-2}$ | 0-150 kg · hm$^{-2}$ | 0-150 kg · hm$^{-2}$ |
| [0.3, 0.5) | 90-240 kg · hm$^{-2}$ | 150-210 kg · hm$^{-2}$ | 150-210 kg · hm$^{-2}$ |
| [0, 0.3) | 240-270 kg · hm$^{-2}$ | 210-270 kg · hm$^{-2}$ | 210-300 kg · hm$^{-2}$ |

If neither of the first identifier information and the second identifier information that are carried by the irrigation instruction is null, that is, current water and fertilizers are all in a moderate state, and both topdressing and watering are required, the irrigation amount and the topdressing amount are converted through the above steps, and the irrigation amount and the topdressing amount are regarded as the water and fertilizer stress decision result to be output.

According to the embodiment of the present disclosure, whether to conduct water and fertilizer irrigation is diagnosed collaboratively on the basis of the fuzzy controller, and the irrigation amount of the water and/or the fertilizers to be implemented in the next cycle is decided and converted according to the identifier information in the output irrigation instruction, such that dynamic collaborative water and fertilizer diagnosis and decision-making are achieved.

On the basis of any one of the above embodiments, the step that the current crop coefficient and canopy temperature of the crop to be identified are determined on the basis of the first crop image and the second crop image includes the following steps: the first crop image is segmented with an excess green algorithm, and a crop canopy image is obtained.

Specifically, in step 101, the decision-making apparatus for water and fertilizer stress of crops segments the first corrected crop image with the excess green algorithm, and extracts a zone having a green color feature, so as to form the crop canopy image.

The crop coefficient is determined according to a canopy coverage ratio analyzed from the crop canopy image.

Specifically, the decision-making apparatus for water and fertilizer stress of crops regards a component ratio of a green canopy zone to the crop canopy image as the canopy coverage ratio, and converts the crop coefficient according to a crop vegetation surface area denoted by the ratio.

The canopy temperature is determined on the basis of the crop canopy image and the second crop image.

Specifically, the decision-making apparatus for water and fertilizer stress of crops merges a visible light template about the canopy zone in the crop canopy image with the second crop image carrying thermal infrared temperature information, so as to extract a temperature of an entire canopy.

According to the embodiment of the present disclosure, the crop canopy image is segmented from the first crop image with the excess green algorithm, the crop coefficient is converted according to the canopy coverage ratio analyzed, and further the crop canopy image is regarded as a template to be merged with the second crop image, such that the canopy temperature is extracted. The thermal infrared and visible light images may be merged, such that the canopy temperature is extracted. Problems that an edge is fuzzy and uncertain when the crop canopy temperature is extracted with the thermal infrared image, and extraction is easily disturbed by an edge temperature are solved.

On the basis of any one of the above embodiments, the step that the canopy temperature is determined on the basis of the crop canopy image and the second crop image includes the following steps: outline coordinates of the crop canopy image and the second crop image are extracted separately with a binary image connected component algorithm, and a first feature point set and a second feature point set are obtained.

Specifically, the decision-making apparatus for water and fertilizer stress of crops classifies the crop canopy image and the second crop image into the same zone and calibrates coordinates. Then, outlines and coordinates are extracted with the binary image connected component algorithm, and edge vertex coordinates in the crop canopy image and the second crop image are regarded as calibration feature points, such that the first feature point set and the second feature point set are formed.

An infrared canopy image is obtained by matching the first feature point set and the second feature point set, and then the canopy temperature is extracted from the infrared canopy image.

Specifically, the decision-making apparatus for water and fertilizer stress of crops conducts registration with the first feature point set and the second feature point set, eliminates geometric distortion between the visible light image and the thermal infrared image through an affine transformation method, and fuses them to obtain infrared canopy image, and conducts merging to obtain the infrared canopy image. A corresponding infrared temperature value is extracted from each pixel point having a pixel value unequal to 0 in the infrared canopy image, and further the canopy temperature corresponding to the entire canopy zone is generated.

Affine transformation means that in geometry, a vector space is transformed linearly and then translated into another vector space. Affine transformation is spatial transformation superimposed by linear transformation and translation transformation, and has spatial changes including spatial position changes such as translation, rotation and scaling.

For any pair of visible light reference calibration feature point (x, y) and thermal infrared calibration feature point (x', y') in the first feature point set and the second feature point set, a mathematical expression of affine transformation from (x, y) to (x', y) is:

$$\begin{bmatrix} x' \\ y' \end{bmatrix} = x \begin{bmatrix} \cos\theta \\ \sin\theta \end{bmatrix} + y \begin{bmatrix} -\sin\theta \\ \cos\theta \end{bmatrix} + \begin{bmatrix} t_x \\ t_y \end{bmatrix} \quad (4)$$

θ is a rotation angle, $t_x$ is an offset of a new coordinate origin from an original coordinate point x, and $t_y$ is an offset of the new coordinate origin from an original coordinate origin y.

According to the embodiment of the present disclosure, the outlines of the crop canopy image and the second crop image are extracted separately, the infrared canopy image is obtained through registration with the first feature point set and the second feature point set that are extracted, and further the canopy temperature is extracted. The edge vertex coordinates may be extracted with the binary image connected component algorithm, and a transformation parameter model between the vertex coordinates may be quickly created through affine transformation, such that a feature point mismatch probability is reduced, and the canopy temperature is accurately extracted.

On the basis of any one of the above embodiments, the step that the crop coefficient is determined according to the canopy coverage ratio analyzed from the crop canopy image includes the following steps: the crop canopy image is input into an analytical model, and the crop coefficient output from the analytical model is obtained.

The analytical model is trained according to a sample crop canopy image and a canopy coverage ratio label and a crop coefficient label that are set in the sample crop canopy image. The analytical model includes a ratio conversion layer and a ratio analysis layer.

The ratio conversion layer is configured to determine the canopy coverage ratio on the basis of the crop canopy image.

The ratio analysis layer is configured to estimate the crop coefficient on the basis of the canopy coverage ratio.

It should be noted that the analytical model may be an artificial intelligence model, and the embodiment of the present disclosure has no specific limit on a model type.

For example, the analytical model may be a neural network, and a structure and parameters of the neural network include, but are not limited to, the number of input layers, the number of hidden layers and the number of output layers of the neural network, and a weight parameter of each layer. The embodiment of the present disclosure has no specific limit on types and structures of the neural network.

For example, the analytical model may be a feedforward neural network. The model consists of an input layer, a hidden layer, and an output layer The input layer is located at a forefront of the entire network and directly receives the crop canopy image.

The number of the hidden layers may be one or more. The hidden layer computes input vectors with its own neurons through weighted summation. A computation formula may be expressed as follows:

$$z = b + w1*x1 + w2*x2 + \ldots + wm*xm,$$

where z denotes the sum of weights output from the hidden layer, x1, x2, x3 ... xm denote m feature vectors of each sample, b denotes an offset, and w1, w2 .... Wm denote weights corresponding to all the feature vectors.

The output layer is the last layer, and is configured to decode vectors obtained through weighted summation and output a crop coefficient corresponding to a canopy feature in the crop canopy image.

It should be noted that sample data includes the sample crop canopy image corresponding to the sample data, and the canopy coverage ratio label and the crop coefficient label marked on the sample crop canopy image in advance. The sample data is divided into a training set and a test set according to a certain ratio.

For example, after the sample data is out of order, the sample data is divided into a training set, a validation set and a test set according to a ratio of 6:2:2.

Specifically, the decision-making apparatus for water and fertilizer stress of crops initializes a weight coefficient of each layer of the constructed analytical model, then inputs a set of sample data in the training set into the neural network under the current weight coefficient, and sequentially computes output of each node of the input layer, the hidden layer, and the output layer. According to a cumulative error between a final output result of the output layer and a state type of an actual connection position, the weight coefficient between each node of the input layer and each node of the hidden layer is corrected through a gradient descent method. According to the above process, the weight coefficients of the input layer and the hidden layer may be obtained until all samples in the training set are traversed.

The decision-making apparatus for water and fertilizer stress of crops restores the analytical model according to the weight coefficients of the input layer and the hidden layer of the neural network, inputs each crop canopy image in the test set into the trained analytical model, and the corresponding crop coefficient analyzed is regarded as an analytical result to be output.

The embodiment of the present disclosure has no specific limit on the analytical model.

Preferably, the analytical model may intelligently explore an optimal model parameter with a bayesian optimization algorithm and input the parameter into an XGBoost algorithm, such that an optimal model for estimating the crop coefficient is obtained. The bayesian optimization algorithm is to fit an objective function with a probability proxy model in an optimization process, and select a next evaluation point according to a previous sampling result, such that an optimal solution may be quickly achieved. The XGBoost algorithm generates a weak learner by optimizing a structured loss function (a loss function added with regular terms may reduce a risk of over-fitting), and the XGBoost algorithm directly uses a first derivative value and a second derivative value of the loss function instead of a search method, such that performance of the algorithm is greatly improved through pre-sorting, weighted quantile and other technologies. The hidden layer at least includes a ratio conversion layer and a ratio analysis layer.

The ratio conversion layer may use a ratio of a canopy pixel zone to the entire crop canopy image as the canopy coverage ratio.

The ratio analysis layer may obtain the corresponding crop coefficient according to a mapping relation between the canopy coverage ratio and the crop coefficient.

According to the embodiment of the present disclosure, the crop canopy image is regarded as input of the analytical model, the ratio conversion layer extracts the canopy coverage ratio from the crop canopy image, and then the ratio analysis layer converts the crop coefficient according to the canopy coverage ratio, such that computation accuracy and efficiency of the crop coefficient are improved.

On the basis of any one of the above embodiments, the step that the water stress state and the nutrient stress state are determined on the basis of the crop coefficient and the canopy temperature of the crop to be identified includes the following step: a crop water stress index determined according to the canopy temperature is set as the water stress state.

Specifically, in step 102, the decision-making apparatus for water and fertilizer stress of crops computes the crop water stress index (CWSI) according to the canopy temperature obtained in step 101, and determines the water stress state according to the CWSI. A computation formula of the CWSI is as follows:

$$CWSI = \frac{T_C - (T_{min} - 2)}{T_{max} + 5 - (T_{min} - 2)} \quad (5)$$

$T_c$ denotes an average crop canopy temperature in units of ° C. $T_{min}$ denotes a minimum average canopy temperature in units of ° C. $T_{max}$ denotes a maximum average canopy temperature in units of ° C.

A normalized difference vegetation index determined according to the crop coefficient is set as the nutrient stress state.

Specifically, the decision-making apparatus for water and fertilizer stress of crops computes the normalized difference vegetation index (NDVI) according to the crop coefficient obtained in step 101, and determines a stress state of a fertilizer (nitrogen) according to the NDVI.

The embodiment of the present disclosure has no specific limit on a computation method for the NDVI.

Figure 2:
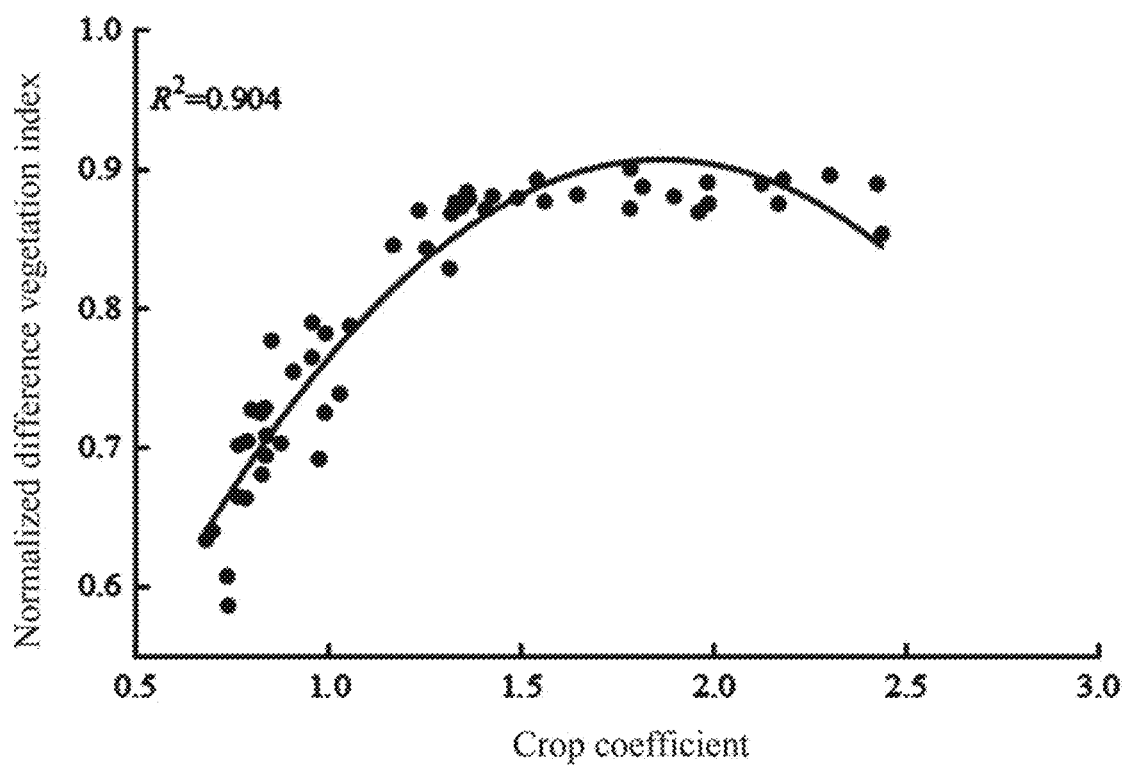
FIG. 2 is a schematic simulation diagram of a normalized difference vegetation index according to the present disclosure.

For example, FIG. 2 is a schematic simulation diagram of a normalized difference vegetation index according to the present disclosure. As shown in FIG. 2, the embodiment of the present disclosure may deploy a large amount of prior data in the form of discrete points in a coordinate system having crop coefficients as the abscissae and NDVIs as ordinates. After linear fitting of the discrete points, a computation formula of the NDVI is as follows:

$$NDVI = -0.191 K_c^2 + 0.712 K_c + 0.243 \quad (6)$$

NDVI is the normalized difference vegetation index, and Kc is the crop coefficient.

Figure 3:
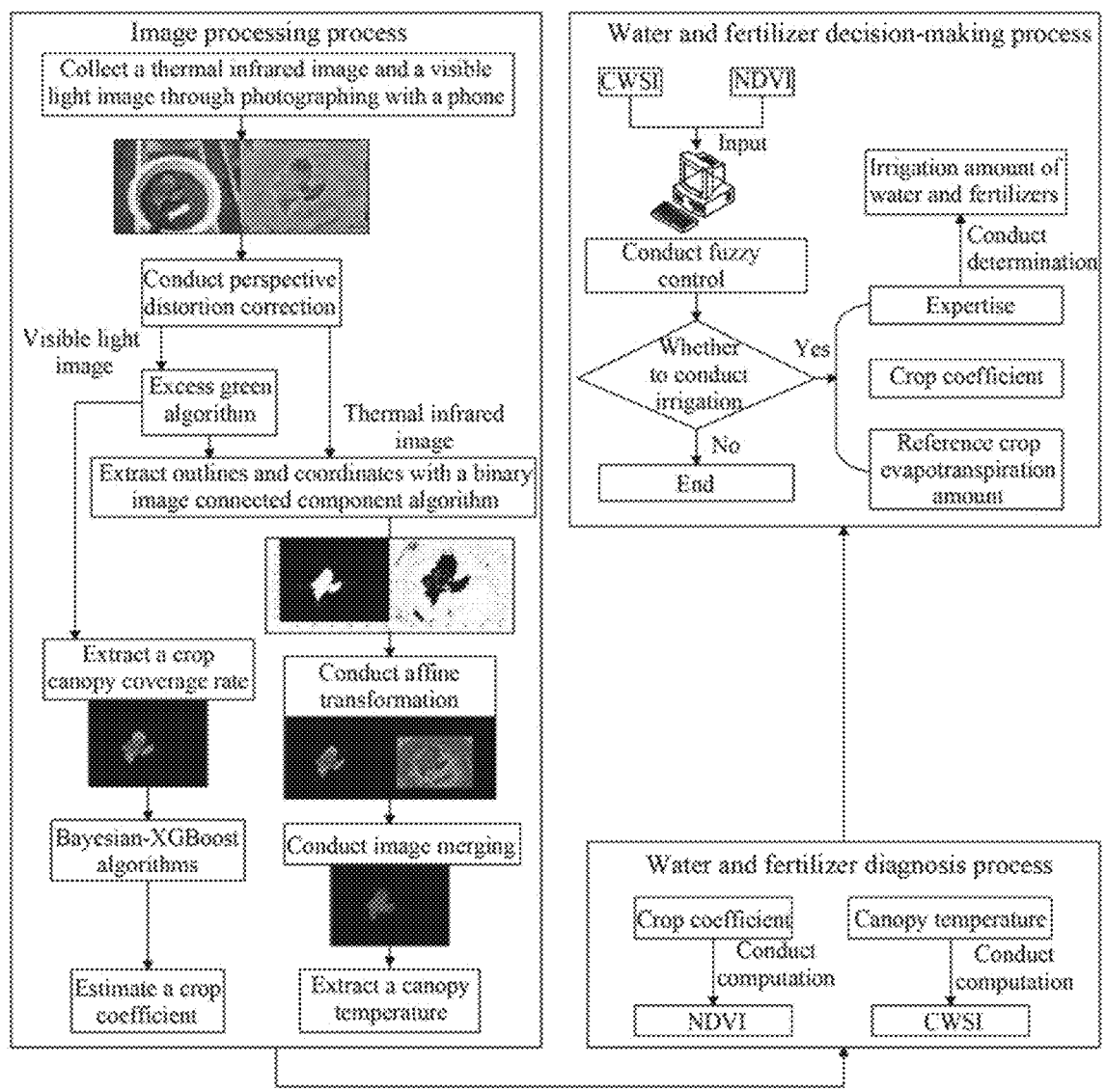
FIG. 3 is a second schematic flow diagram of a decision-making method for water and fertilizer stress of crops according to the present disclosure.

For example, FIG. 3 is a second schematic flow diagram of a decision-making method for water and fertilizer stress of crops according to the present disclosure. As shown in FIG. 3, a specific implementation mode of the decision-making method for water and fertilizer stress of crops according to the embodiment of the present disclosure is as follows:

(1) Image Processing Process

A visible light image and a thermal infrared image of a crop are obtained through photographing with a phone, the collected images are corrected through perspective distortion correction, and then related algorithm processing is conducted on the basis of the corrected images, such that a crop coefficient and canopy temperature are obtained in real time.

(2) Water and Fertilizer Diagnosis Process

According to the crop coefficient and the canopy temperature that are obtained in the image processing process, a crop water stress index (CWSI) is obtained from the canopy temperature extracted from the merged visible light image and thermal infrared image, and a water stress state is determined according to the CWSI.

In addition, a fertilizer diagnosis model is created according to the crop coefficient and an NDVI that are obtained on the basis of a canopy coverage rate extracted from the visible light image, the NDVI is computed according to the model, and a stress state of a fertilizer (nitrogen) is determined according to the NDVI.

(3) Water and Fertilizer Decision-Making Process

The CWSI and the NDVI computed in the water and fertilizer diagnosis process are regarded as input variables of a fuzzy controller, and are provided in natural language instead of a numerical form. On the basis of a decision-making rule obtained through the above fuzzy decision-making, whether to conduct irrigation and an irrigation amount of water and fertilizers are determined. An irrigation amount of water is obtained by multiplying the crop coefficient obtained on the basis of the canopy coverage rate extracted from the visible light image by a reference crop evapotranspiration amount. A topdressing amount of the fertilizers is determined according to expertise.

According to the embodiment of the present disclosure, the crop water stress index converted from the canopy temperature is configured to represent the water stress state, and the normalized difference vegetation index converted from the crop coefficient is configured to represent a nutrient stress state. Dynamic determination may be conducted on the water stress state and the nutrient stress state according to a growth situation of crops, and decision-making accuracy is improved.

On the basis of any one of the above embodiments, after the water stress state and the nutrient stress state are processed with the fuzzy control algorithm, and the water and fertilizer stress decision result of the crop to be identified is determined, the method further includes the following steps: in response to determining that the water and fertilizer stress decision result only includes the irrigation amount, an irrigation apparatus is controlled to add water of the irrigation amount to the crop to be identified in the next cycle according to a first control instruction;

in response to determining that the water and fertilizer stress decision result only includes the topdressing amount, a fertilization apparatus is controlled to add fertilizers of the topdressing amount to the crop to be identified in the next cycle according to a second control instruction; and in response to determining that the water and fertilizer stress decision result includes both the irrigation amount and the topdressing amount, an irrigation apparatus is controlled to add water of the irrigation amount to the crop to be identified in the next cycle according to a third control instruction, and meanwhile, a fertilization apparatus is controlled to add fertilizers of the topdressing amount to the crop to be identified in the next cycle.

Specifically, in step 104, the decision-making apparatus for water and fertilizer stress of crops controls the irrigation apparatus and/or the fertilization apparatus to execute corresponding decision-making measures in the next cycle according to the water and fertilizer stress decision result.

If the water and fertilizer stress decision result only includes the irrigation amount, that is, only watering without topdressing is required in the next cycle, the irrigation amount is encapsulated in the first control instruction and then transmitted to the irrigation apparatus. Accordingly, the irrigation apparatus may receive and respond to the first control instruction so as to add water of the irrigation amount to the crop to be identified in the next cycle.

If the water and fertilizer stress decision result only includes the topdressing amount, that is, only topdressing without watering is required in the next cycle, the topdressing amount is encapsulated in the second control instruction and then transmitted to the irrigation apparatus. Accordingly, the fertilization apparatus may receive and respond to the second control instruction so as to add fertilizers of the topdressing amount to the crop to be identified in the next cycle.

If the water and fertilizer stress decision result includes both the irrigation amount and topdressing amount, that is, both topdressing and watering are required in the next cycle, the irrigation amount is encapsulated in the first control instruction, the topdressing amount is encapsulated in the second control instruction, and then the control instructions are transmitted to the corresponding apparatuses. Accordingly, the irrigation apparatus may receive and respond to the first control instruction so as to add water of the irrigation amount to the crop to be identified in the next cycle. Meanwhile, the fertilization apparatus may receive and respond to the second control instruction so as to add fertilizers of the topdressing amount to the crop to be identified in the next cycle.

The embodiment of the present disclosure makes a decision to control corresponding executing apparatuses to conduct irrigation and/or topdressing according to different control instructions by analyzing the water and fertilizer stress decision result. The present disclosure may achieve dynamic collaborative water and fertilizer diagnosis and decision-making through an image collection means having high flexibility and low cost, and automatically controls the corresponding apparatuses to execute irrigation operations, such that agricultural integration and automation is facilitated.

Figure 4:
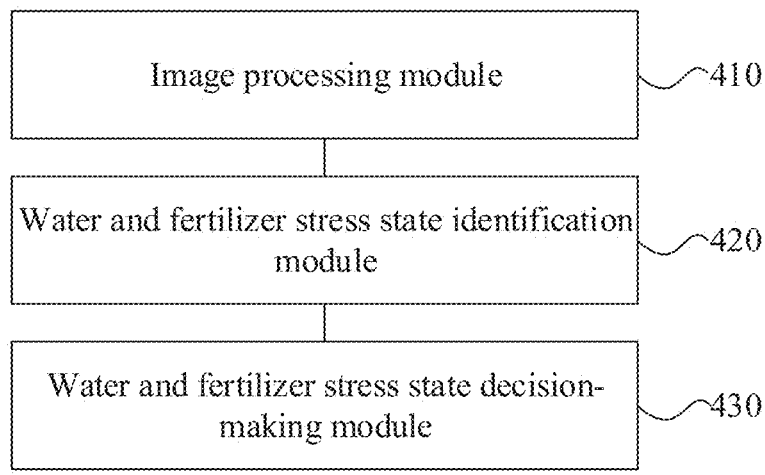
FIG. 4 is a schematic structural diagram of a decision-making apparatus for water and fertilizer stress of crops according to the present disclosure.

FIG. 4 is a schematic structural diagram of a decision-making apparatus for water and fertilizer stress of crops according to the present disclosure. On the basis of any one of the above embodiments, as shown in FIG. 4, the apparatus includes an image processing module 410, a water and fertilizer stress state identification module 420, and a water and fertilizer stress state decision-making module 430.

The image processing module 410 is configured to determine a current crop coefficient and canopy temperature of a crop to be identified on the basis of a first crop image and a second crop image.

The water and fertilizer stress state identification module 420 is configured to determine a water stress state and a nutrient stress state on the basis of the current crop coefficient and canopy temperature of the crop to be identified.

The water and fertilizer stress state decision-making module 430 is configured to process the water stress state and the nutrient stress state with a fuzzy control algorithm, and determine a water and fertilizer stress decision result of the crop to be identified.

The decision result includes an irrigation amount and/or a topdressing amount for the crop to be identified in a next cycle. The first crop image is a visible light image obtained by photographing the crop to be identified in full view with a terminal. The second crop image is a thermal infrared image obtained by photographing the crop to be identified in full view with an infrared module connected to the terminal.

Specifically, the image processing module 410, the water and fertilizer stress state identification module 420 and the water and fertilizer stress state decision-making module 430 are electrically connected in sequence.

The image processing module 410 receives the first crop image and the second crop image collected by a photographing module and an infrared module arranged on a mobile phone terminal in a current working cycle respectively, conducts a related image algorithm on the received images, and completely separates a canopy zone of the crop. Further, the crop coefficient and the canopy temperature corresponding to each pixel point in the canopy zone are converted.

The water and fertilizer stress state identification module 420 converts and maps influence of objective factors such as a climate condition, groundwater drought and a plant root size on crop water management to the water stress state according to a ratio of a water demand to a possible evapotranspiration amount and outputs the water stress state. The ratio is denoted by the crop coefficient obtained in step 101.

The water and fertilizer stress state decision-making module 430 determines each irrigation decision index under combined action of the water stress state and the nutrient stress state with a membership function in the fuzzy control algorithm, and further conducts irrigation decision-making with a pre-created fuzzy rule, so as to obtain the water and fertilizer stress decision result of the crop to be identified.

The water and fertilizer stress decision result is determined according to a fuzzy rule that may balance water and fertilizers at a basic level in the next cycle.

Alternatively, the water and fertilizer stress state decision-making module 430 includes a fuzzy control unit and a decision-making unit.

The fuzzy control unit is configured to convert the water stress state and the nutrient stress state into linguistic variables, input the linguistic variables into a fuzzy controller, and obtain an irrigation instruction output from the fuzzy controller.

The decision-making unit is configured to set, in response to determining that first identifier information and second identifier information that are carried by the irrigation instruction are non-null and null respectively, an irrigation amount determined according to the crop coefficient and a reference crop evapotranspiration amount as the water and fertilizer stress decision result.

The decision-making unit is further configured to set, in response to determining that first identifier information and second identifier information that are carried by the irrigation instruction are null and non-null respectively, a topdressing amount determined according to the nutrient stress state and species information of the crop to be identified as the water and fertilizer stress decision result.

The decision-making unit is further configured to set, in response to determining that neither of first identifier information and second identifier information carried by the irrigation instruction is null, an irrigation amount determined according to the crop coefficient and a reference crop evapotranspiration amount and a topdressing amount determined according to the nutrient stress state and species information of the crop to be identified as the water and fertilizer stress decision result.

The fuzzy controller is created on the basis of a corresponding fuzzy rule between an input fuzzy set and an output fuzzy set. The input fuzzy set is determined according to a membership function set on the basis of fuzzy scales obtained by conducting fuzzy division on the water stress state and the nutrient stress state. The output fuzzy set is determined according to a membership function set on the basis of strategy scales of a plurality of water and fertilizer stress states obtained by clarifying a fuzzy language. The fuzzy rule is created by determining corresponding water and fertilizer stress states according to different water stress states and nutrient stress states. Identifier information carried by the irrigation instruction is determined according to the water and fertilizer stress state. The first identifier information is configured to indicate whether to conduct irrigation. The second identifier information is configured to indicate whether to conduct topdressing.

Alternatively, the image processing module 410 includes a segmentation unit, a crop coefficient obtaining unit, and a canopy temperature obtaining unit.

The segmentation unit is configured to segment the first crop image with an excess green algorithm, and obtain a crop canopy image.

The crop coefficient obtaining unit is configured to determine the crop coefficient according to a canopy coverage ratio analyzed from the crop canopy image.

The canopy temperature obtaining unit is configured to determine the canopy temperature on the basis of the crop canopy image and the second crop image.

Alternatively, the canopy temperature obtaining unit includes a feature point calibration subunit and a feature point registration subunit.

The feature point calibration subunit is configured to extract outline coordinates of the crop canopy image and the second crop image separately with a binary image connected component algorithm, and obtain a first feature point set and a second feature point set.

The feature point registration subunit is configured to obtain an infrared canopy image by matching the first feature point set and the second feature point set, and then extract the canopy temperature from the infrared canopy image.

Alternatively, the crop coefficient obtaining unit is specifically configured to input the crop canopy image into an analytical model, and obtain the crop coefficient output from the analytical model.

The analytical model is trained according to a sample crop canopy image and a canopy coverage ratio label and a crop coefficient label that are set in the sample crop canopy image. The analytical model includes a ratio conversion layer and a ratio analysis layer.

The ratio conversion layer is configured to determine the canopy coverage ratio on the basis of the crop canopy image.

The ratio analysis layer is configured to estimate the crop coefficient on the basis of the canopy coverage ratio.

Alternatively, the water and fertilizer stress state identification module 420 includes a water stress state diagnosis unit and a nutrient stress state diagnosis unit.

The water stress state diagnosis unit is configured to set a crop water stress index determined according to the canopy temperature as the water stress state.

The nutrient stress state diagnosis unit is configured to set a normalized difference vegetation index determined according to the crop coefficient as the nutrient stress state.

Alternatively, the apparatus further includes a first control module, a second control module, and a third control module.

The first control module is configured to control, in response to determining that the water and fertilizer stress decision result only includes the irrigation amount, an irrigation apparatus to add water of the irrigation amount to the crop to be identified in the next cycle according to a first control instruction.

The second control module is configured to control, in response to determining that the water and fertilizer stress decision result only includes the topdressing amount, a fertilization apparatus to add fertilizers of the topdressing amount to the crop to be identified in the next cycle according to a second control instruction.

The third control module is configured to control, in response to determining that the water and fertilizer stress decision result includes both the irrigation amount and the topdressing amount, an irrigation apparatus to add water of the irrigation amount to the crop to be identified in the next cycle according to a third control instruction, and meanwhile, control a fertilization apparatus to add fertilizers of the topdressing amount to the crop to be identified in the next cycle.

The decision-making apparatus for water and fertilizer stress of crops according to the embodiment of the present disclosure is configured to execute the decision-making method for water and fertilizer stress of crops according to the present disclosure, has a consistent implementation mode with the decision-making method for water and fertilizer stress of crops according to the present disclosure, and may achieve the same beneficial effects, which will not be repeated herein.

Figure 5:
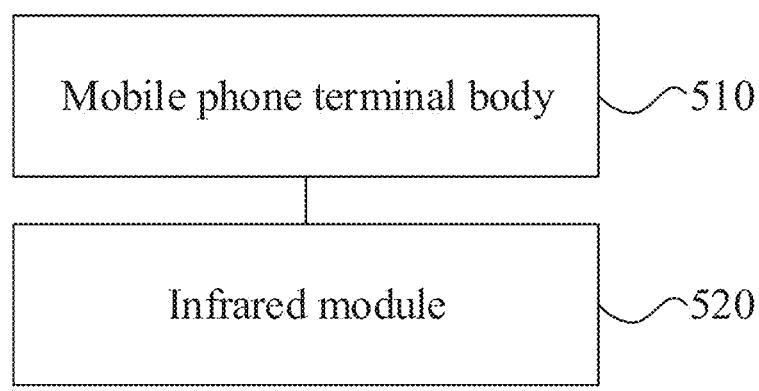
FIG. 5 is a schematic structural diagram of a mobile phone terminal according to the present disclosure.

FIG. 5 is a schematic structural diagram of a mobile phone terminal according to the present disclosure. On the basis of any one of the above embodiments, as shown in FIG. 5, the mobile phone terminal includes a mobile phone terminal body 510 and an infrared module 520 that are in communication connection with each other. The mobile phone terminal body 510 includes a memory, a processor, and a computer program stored in the memory and runnable in the processor. The processor implements the decision-making method for water and fertilizer stress of crops when executing the computer program.

Specifically, the mobile phone terminal consists of the mobile phone terminal body 510 and the infrared module 520 that are in communication connection with each other.

When using the mobile phone terminal, a user drives an imaging module built in the mobile phone terminal body 510 to obtain the first crop image through photographing, and further drives the infrared module 520 to obtain the second crop image through photographing. Further, the above image is transmitted back to the processor of the mobile phone terminal body 510, and the processor executes the decision-making method for water and fertilizer stress of crops. The user is guided to adjust crop maintenance measures in the next cycle according to the water and fertilizer stress decision result.

Figure 6:
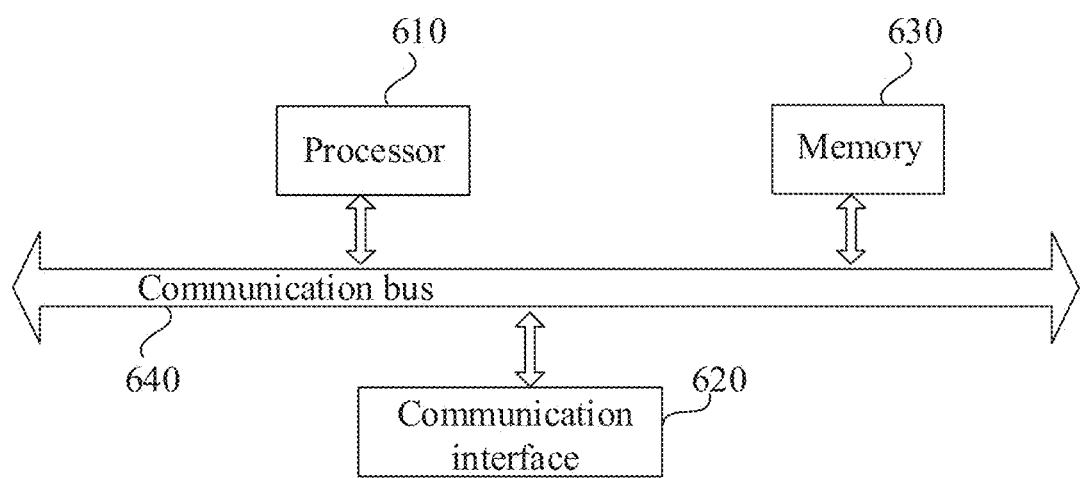
FIG. 6 is a schematic structural diagram of an electronic device according to the present disclosure.

FIG. 6 illustratively shows a schematic diagram of a physical structure of an electronic device. As shown in FIG. 6, the electronic device includes: a processor 610, a communication interface 620, a memory 630, and a communication bus 640. The processor 610, the communication interface 620 and the memory 630 are in communication with one another by means of the communication bus 640. The processor 610 may call a logical instruction in the memory 630, so as to execute the decision-making method for water and fertilizer stress of crops. The method includes the following steps: a current crop coefficient and canopy temperature of a crop to be identified are determined on the basis of a first crop image and a second crop image; a water stress state and a nutrient stress state are determined on the basis of the current crop coefficient and canopy temperature of the crop to be identified; and the water stress state and the nutrient stress state are processed with a fuzzy control algorithm, and a water and fertilizer stress decision result of the crop to be identified is determined. The water and fertilizer stress decision result includes an irrigation amount and/or a topdressing amount for the crop to be identified in a next cycle. The first crop image is a visible light image obtained by photographing the crop to be identified in full view with a terminal. The second crop image is a thermal infrared image obtained by photographing the crop to be identified in full view with an infrared module connected to the terminal.

In addition, the logical instruction in the above memory 630 may be implemented as a software functional unit, and may be stored in a computer-readable storage medium when being sold or used as an independent product. On the basis of such understanding, the technical solution of the present disclosure, in essence or from the view of part contributing to the prior art, or part of the technical solution, may be embodied in the form of a computer software product that is stored in a storage medium and includes a plurality of instructions configured to enable one computer device (which may be a personal computer, a server, a network device, etc.) to execute all or some of the steps of the method in each embodiment of the present disclosure. The above storage medium includes: a USB flash disk, a mobile hard disk, a read-only memory (ROM), a random access memory (RAM), a magnetic disk, an optical disk and other media capable of storing program codes.

In another aspect, the present disclosure further provides a computer program product. The computer program product includes a computer program. The computer program may be stored on a non-transient computer-readable storage medium. When the computer program is executed by a processor, a computer may execute the decision-making method for water and fertilizer stress of crops according to the above methods.

In yet another aspect, the present disclosure further provides a non-transient computer-readable storage medium storing a computer program. The computer program executes the decision-making method for water and fertilizer stress of crops according to the above methods when being executed by a processor.

The apparatus embodiments described above are merely illustrative. Units described as separate components may be physically separated or not, and a component displayed as a unit may o be a physical unit or not. That is, the component may be located at one place, or distributed on a plurality of network units. Some or all of the modules may be selected according to actual needs, so as to achieve the objective of the solution of the embodiments. Those of ordinary skill in the art may understand and implement the present disclosure without making the inventive effort.

From the description of the above implementation modes, those skilled in the art may obviously understand that each implementation mode may be achieved by means of software plus a general-purpose hardware platform, and certainly may also be achieved by means of hardware. On the basis of such understanding, the technical solution of the present disclosure, in essence or from the view of the part contributing to the prior art, may be embodied in the form of a software product. The computer software product may be stored in a computer-readable storage medium (such as ROM/RAM, a magnetic disk and an optical disk) and includes a plurality of instructions configured to enable one computer device (which may be a personal computer, a server, or a network device) to execute the method in all or some of the embodiments of the present disclosure.

Finally, it should be noted that the above embodiments are merely used to describe the technical solution of the present disclosure, rather than limiting the same. Although the present disclosure has been described in detail with reference to the above embodiments, those of ordinary skill in the art should understand that the technical solution described in the above embodiments may still be modified, or some of the technical features therein may be equivalently replaced. However, these modifications or substitutions do not enable the essence of the corresponding technical solutions to deviate from the spirit and scope of the technical solutions of each embodiment of the present disclosure.

What is claimed is:

1. A decision-making method for water and fertilizer stress of crops, comprising:
   determining a current crop coefficient and canopy temperature of a crop to be identified on the basis of a first crop image and a second crop image;
   determining a water stress state and a nutrient stress state on the basis of the current crop coefficient and canopy temperature of the crop to be identified; and
   processing the water stress state and the nutrient stress state with a fuzzy control algorithm, and determining a water and fertilizer stress decision result of the crop to be identified, wherein
   the decision result comprises an irrigation amount and/or a topdressing amount for the crop to be identified in a next cycle; the first crop image is a visible light image obtained by photographing the crop to be identified in full view with a terminal; the second crop image is a thermal infrared image obtained by photographing the crop to be identified in full view with an infrared module connected to the terminal;
   the processing the water stress state and the nutrient stress state with a fuzzy control algorithm, and determining a water and fertilizer stress decision result of the crop to be identified comprises:
   converting the water stress state and the nutrient stress state into linguistic variables, inputting the linguistic variables into a fuzzy controller, and obtaining an irrigation instruction output from the fuzzy controller;
   setting, in response to determining that first identifier information and second identifier information that are carried by the irrigation instruction are non-null and null respectively, an irrigation amount determined according to the crop coefficient and a reference crop evapotranspiration amount as the water and fertilizer stress decision result;

setting, in response to determining that first identifier information and second identifier information that are carried by the irrigation instruction are null and non-null respectively, a topdressing amount determined according to the nutrient stress state and species information of the crop to be identified as the water and fertilizer stress decision result; and setting, in response to determining that neither of first identifier information and second identifier information that are carried by the irrigation instruction is null, an irrigation amount determined according to the crop coefficient and a reference crop evapotranspiration amount and a topdressing amount determined according to the nutrient stress state and species information of the crop to be identified as the water and fertilizer stress decision result; and the fuzzy controller is created on the basis of a corresponding fuzzy rule between an input fuzzy set and an output fuzzy set; the input fuzzy set is determined according to a membership function set on the basis of fuzzy scales obtained by conducting fuzzy division on the water stress state and the nutrient stress state; the output fuzzy set is determined according to a membership function set on the basis of strategy scales of a plurality of water and fertilizer stress states obtained by clarifying a fuzzy language; the fuzzy rule is created by determining corresponding water and fertilizer stress states according to different water stress states and nutrient stress states; identifier information carried by the irrigation instruction is determined according to the water and fertilizer stress state; the first identifier information is configured to indicate whether to conduct irrigation; and the second identifier information is configured to indicate whether to conduct topdressing.

2. The decision-making method for water and fertilizer stress of crops according to claim 1, wherein the determining a current crop coefficient and canopy temperature of a crop to be identified on the basis of a first crop image and a second crop image comprises:

segmenting the first crop image with an excess green algorithm, and obtaining a crop canopy image;

determining the crop coefficient according to a canopy coverage ratio analyzed from the crop canopy image; and determining the canopy temperature on the basis of the crop canopy image and the second crop image.

3. The decision-making method for water and fertilizer stress of crops according to claim 2, wherein the determining the canopy temperature on the basis of the crop canopy image and the second crop image comprises:

extracting outline coordinates of the crop canopy image and the second crop image separately with a binary image connected component algorithm, and obtaining a first feature point set and a second feature point set; and obtaining an infrared canopy image by matching the first feature point set and the second feature point set, and then extracting the canopy temperature from the infrared canopy image.

4. The decision-making method for water and fertilizer stress of crops according to claim 2, wherein the determining the crop coefficient according to a canopy coverage ratio analyzed from the crop canopy image comprises:

inputting the crop canopy image into an analytical model, and obtaining the crop coefficient output from the analytical model, wherein the analytical model is trained according to a sample crop canopy image and a canopy coverage ratio label and a crop coefficient label that are set in the sample crop canopy image; the analytical model comprises a ratio conversion layer and a ratio analysis layer;

the ratio conversion layer is configured to determine the canopy coverage ratio on the basis of the crop canopy image; and the ratio analysis layer is configured to estimate the crop coefficient on the basis of the canopy coverage ratio.

5. The decision-making method for water and fertilizer stress of crops according to claim 1, wherein the determining a water stress state and a nutrient stress state on the basis of the crop coefficient and canopy temperature of the crop to be identified comprises:

setting a crop water stress index determined according to the canopy temperature as the water stress state; and setting a normalized difference vegetation index determined according to the crop coefficient as the nutrient stress state.

6. The decision-making method for water and fertilizer stress of crops according to claim 1, wherein after the processing the water stress state and the nutrient stress state with a fuzzy control algorithm and determining a water and fertilizer stress decision result of the crop to be identified, the method further comprises:

controlling, in response to determining that the water and fertilizer stress decision result only comprises the irrigation amount, an irrigation apparatus to add water of the irrigation amount to the crop to be identified in the next cycle according to a first control instruction;

controlling, in response to determining that the water and fertilizer stress decision result only comprises the topdressing amount, a fertilization apparatus to add fertilizers of the topdressing amount to the crop to be identified in the next cycle according to a second control instruction; and controlling, in response to determining that the water and fertilizer stress decision result only comprises the topdressing amount, an irrigation apparatus to add water of the irrigation amount to the crop to be identified in the next cycle according to a third control instruction, and a fertilization apparatus to add fertilizers of the topdressing amount to the crop to be identified in the next cycle.

7. A mobile phone terminal, comprising a mobile phone terminal body and an infrared module that are in communication connection with each other, wherein the mobile phone terminal body comprises a memory, a processor, and a computer program stored in the memory and runnable in the processor, and the processor implements the decision-making method for water and fertilizer stress of crops according to claim 1 when executing the computer program.

8. The mobile phone terminal according to claim 7, wherein the determining a current crop coefficient and canopy temperature of a crop to be identified on the basis of a first crop image and a second crop image comprises:

segmenting the first crop image with an excess green algorithm, and obtaining a crop canopy image;

determining the crop coefficient according to a canopy coverage ratio analyzed from the crop canopy image; and determining the canopy temperature on the basis of the crop canopy image and the second crop image.

9. The mobile phone terminal according to claim 8, wherein the determining the canopy temperature on the basis of the crop canopy image and the second crop image comprises:

extracting outline coordinates of the crop canopy image and the second crop image separately with a binary image connected component algorithm, and obtaining a first feature point set and a second feature point set; and obtaining an infrared canopy image by matching the first feature point set and the second feature point set, and then extracting the canopy temperature from the infrared canopy image.

10. The mobile phone terminal according to claim 8, wherein the determining the crop coefficient according to a canopy coverage ratio analyzed from the crop canopy image comprises:

inputting the crop canopy image into an analytical model, and obtaining the crop coefficient output from the analytical model, wherein the analytical model is trained according to a sample crop canopy image and a canopy coverage ratio label and a crop coefficient label that are set in the sample crop canopy image; the analytical model comprises a ratio conversion layer and a ratio analysis layer;

the ratio conversion layer is configured to determine the canopy coverage ratio on the basis of the crop canopy image; and the ratio analysis layer is configured to estimate the crop coefficient on the basis of the canopy coverage ratio.

11. The mobile phone terminal according to claim 7, wherein the determining a water stress state and a nutrient stress state on the basis of the crop coefficient and canopy temperature of the crop to be identified comprises:

setting a crop water stress index determined according to the canopy temperature as the water stress state; and setting a normalized difference vegetation index determined according to the crop coefficient as the nutrient stress state.

12. The mobile phone terminal according to claim 7, wherein after the processing the water stress state and the nutrient stress state with a fuzzy control algorithm and determining a water and fertilizer stress decision result of the crop to be identified, the method further comprises:

controlling, in response to determining that the water and fertilizer stress decision result only comprises the irrigation amount, an irrigation apparatus to add water of the irrigation amount to the crop to be identified in the next cycle according to a first control instruction;

controlling, in response to determining that the water and fertilizer stress decision result only comprises the topdressing amount, a fertilization apparatus to add fertilizers of the topdressing amount to the crop to be identified in the next cycle according to a second control instruction; and controlling, in response to determining that the water and fertilizer stress decision result only comprises the topdressing amount, an irrigation apparatus to add water of the irrigation amount to the crop to be identified in the next cycle according to a third control instruction, and a fertilization apparatus to add fertilizers of the topdressing amount to the crop to be identified in the next cycle.

13. A non-transient computer-readable storage medium, storing a computer program, wherein the computer program implements the decision-making method for water and fertilizer stress of crops according to claim 1 when being executed by a processor.

14. The non-transient computer-readable storage medium according to claim 13, wherein the determining a current crop coefficient and canopy temperature of a crop to be identified on the basis of a first crop image and a second crop image comprises:

segmenting the first crop image with an excess green algorithm, and obtaining a crop canopy image;

determining the crop coefficient according to a canopy coverage ratio analyzed from the crop canopy image; and determining the canopy temperature on the basis of the crop canopy image and the second crop image.

15. The non-transient computer-readable storage medium according to claim 14, wherein the determining the canopy temperature on the basis of the crop canopy image and the second crop image comprises:

extracting outline coordinates of the crop canopy image and the second crop image separately with a binary image connected component algorithm, and obtaining a first feature point set and a second feature point set; and obtaining an infrared canopy image by matching the first feature point set and the second feature point set, and then extracting the canopy temperature from the infrared canopy image.

16. The non-transient computer-readable storage medium according to claim 14, wherein the determining the crop coefficient according to a canopy coverage ratio analyzed from the crop canopy image comprises:

inputting the crop canopy image into an analytical model, and obtaining the crop coefficient output from the analytical model, wherein the analytical model is trained according to a sample crop canopy image and a canopy coverage ratio label and a crop coefficient label that are set in the sample crop canopy image; the analytical model comprises a ratio conversion layer and a ratio analysis layer;

the ratio conversion layer is configured to determine the canopy coverage ratio on the basis of the crop canopy image; and the ratio analysis layer is configured to estimate the crop coefficient on the basis of the canopy coverage ratio.

17. The non-transient computer-readable storage medium according to claim 13, wherein the determining a water stress state and a nutrient stress state on the basis of the crop coefficient and canopy temperature of the crop to be identified comprises:

setting a crop water stress index determined according to the canopy temperature as the water stress state; and setting a normalized difference vegetation index determined according to the crop coefficient as the nutrient stress state.

18. The non-transient computer-readable storage medium according to claim 13, wherein after the processing the water stress state and the nutrient stress state with a fuzzy control algorithm and determining a water and fertilizer stress decision result of the crop to be identified, the method further comprises:

controlling, in response to determining that the water and fertilizer stress decision result only comprises the irrigation amount, an irrigation apparatus to add water of the irrigation amount to the crop to be identified in the next cycle according to a first control instruction;

controlling, in response to determining that the water and fertilizer stress decision result only comprises the topdressing amount, a fertilization apparatus to add fertilizers of the topdressing amount to the crop to be identified in the next cycle according to a second control instruction; and controlling, in response to determining that the water and fertilizer stress decision result only comprises the topdressing amount, an irrigation apparatus to add water of the irrigation amount to the crop to be identified in the next cycle according to a third control instruction, and a fertilization apparatus to add fertilizers of the topdressing amount to the crop to be identified in the next cycle.

19. A decision-making apparatus for water and fertilizer stress of crops, comprising:

an image processing module configured to determine a current crop coefficient and canopy temperature of a crop to be identified on the basis of a first crop image and a second crop image;

a water and fertilizer stress state identification module configured to determine a water stress state and a nutrient stress state on the basis of the current crop coefficient and canopy temperature of the crop to be identified; and a water and fertilizer stress state decision-making module configured to process the water stress state and the nutrient stress state with a fuzzy control algorithm, and determine a water and fertilizer stress decision result of the crop to be identified, wherein the decision result comprises an irrigation amount and/or a topdressing amount for the crop to be identified in a next cycle; the first crop image is a visible light image obtained by photographing the crop to be identified in full view with a terminal; the second crop image is a thermal infrared image obtained by photographing the crop to be identified in full view with an infrared module connected to the terminal; and the water and fertilizer stress state decision-making module comprises a fuzzy control unit and a decision-making unit, wherein the fuzzy control unit is configured to convert the water stress state and the nutrient stress state into linguistic variables, input the linguistic variables into a fuzzy controller, and obtain an irrigation instruction output from the fuzzy controller;

the decision-making unit is configured to set, in response to determining that first identifier information and second identifier information that are carried by the irrigation instruction are non-null and null respectively, an irrigation amount determined according to the crop coefficient and a reference crop evapotranspiration amount as the water and fertilizer stress decision result;

the decision-making unit is further configured to set, in response to determining that first identifier information and second identifier information that are carried by the irrigation instruction are null and non-null respectively, a topdressing amount determined according to the nutrient stress state and species information of the crop to be identified as the water and fertilizer stress decision result; and the decision-making unit is further configured to set, in response to determining that neither of first identifier information and second identifier information that are carried by the irrigation instruction is null, an irrigation amount determined according to the crop coefficient and a reference crop evapotranspiration amount and a topdressing amount determined according to the nutrient stress state and species information of the crop to be identified as the water and fertilizer stress decision result, wherein the fuzzy controller is created on the basis of a corresponding fuzzy rule between an input fuzzy set and an output fuzzy set; the input fuzzy set is determined according to a membership function set on the basis of fuzzy scales obtained by conducting fuzzy division on the water stress state and the nutrient stress state; the output fuzzy set is determined according to a membership function set on the basis of strategy scales of a plurality of water and fertilizer stress states obtained by clarifying a fuzzy language; the fuzzy rule is created by determining corresponding water and fertilizer stress states according to different water stress states and nutrient stress states; identifier information carried by the irrigation instruction is determined according to the water and fertilizer stress state; the first identifier information is configured to indicate whether to conduct irrigation; and the second identifier information is configured to indicate whether to conduct topdressing.

* * * * *